United States Patent [19]

Wunderlich et al.

[11] Patent Number: 5,384,129
[45] Date of Patent: Jan. 24, 1995

[54] PELLETS CONTAINING DIHYDROPYRIDINE DERIVATIVES PROCESS FOR THE PRODUCTION THEREOF AND USE AS RAPID ACTION DOSAGE IN HEART AND CIRCULATORY DISEASES

[75] Inventors: Jens-Christian Wunderlich, Heidelberg; Ursula Schick, Wiesloch; Jurgen Freidenreich, Schriesheim; Jurgen Werry, Ludwigshafen, all of Germany

[73] Assignee: ALFATEC Pharma GmbH, Heidelberg, Germany

[21] Appl. No.: 876,877

[22] Filed: Apr. 30, 1992

[30] Foreign Application Priority Data

Jan. 17, 1992 [DE] Germany .............................. 4201173

[51] Int. Cl.$^6$ ......................... A61K 9/48; A61K 9/20; A01N 65/00
[52] U.S. Cl. .................................. 424/451; 424/456; 424/484; 424/485; 424/464; 424/486; 424/492; 424/195.1; 424/520
[58] Field of Search ............... 424/401, 408, 456, 484, 424/485, 486, 492, 520, 195.1, 451, 464; 514/303

[56] References Cited

U.S. PATENT DOCUMENTS

| | | | |
|---|---|---|---|
| 3,691,281 | 9/1972 | Battista | 424/195.1 |
| 4,470,202 | 9/1984 | Buxton et al. | 34/5 |
| 4,758,437 | 7/1988 | Sonobe et al. | 424/501 |
| 4,892,741 | 1/1990 | Ohm et al. | 424/482 |
| 4,933,186 | 6/1990 | Ohm et al. | 424/476 |
| 4,963,560 | 10/1990 | Cooper et al. | 514/303 |
| 5,019,400 | 5/1991 | Gombotz et al. | 424/497 |

FOREIGN PATENT DOCUMENTS 0362582  11/1990  European Pat. Off. .

*Primary Examiner*—Thurman K. Page
*Assistant Examiner*—Peter F. Kulkosky
*Attorney, Agent, or Firm*—Omri M. Behr; Matthew J. McDonald

[57] ABSTRACT

The present invention is directed to dihydropyridine derivative containing pellets comprising a dispersion of the dihydropyridine derivatives in a matrix which is substantially formed of a skeleton builder such as gelatin, fractionated gelatin, a collagen hydrolysate and/or a gelatin derivative. The invention further directs to a process for the preparation of dihydropyridine derivative containing pellets as well as their use as acute dosage forms against heart/circulatory illnesses.

19 Claims, 1 Drawing Sheet

PELLETS CONTAINING DIHYDROPYRIDINE DERIVATIVES PROCESS FOR THE PRODUCTION THEREOF AND USE AS RAPID ACTION DOSAGE IN HEART AND CIRCULATORY DISEASES

FIELD OF THE INVENTION

The present invention is directed to dihydropyridine derivatives containing tablets comprising a dispersion of the dihydropyridine derivatives in a matrix which comprises principally of a skeleton builder, suitably gelatin, fractionated gelatin, a collagen hydrolysate and/or a gelatin derivative. The invention further is directed to a process for the production of dihydropyridine derivative containing tablets as well as their use as acute dosage forms against heart/circulatory diseases.

BACKGROUND OF THE INVENTION

Dihydropyridine derivatives belong to the pharmacological class known as calcium antagonists. They are indicated in a plurality of heart/circulatory diseases, for example, coronary heart disease, arterial hypertension, angina pectoris and so on. The prescription of over 700 million defined daily doses in the year 1989 clearly shows the market position of this class of substances. The first member of this group is Nifedipin (1,4-dihydro-2,6,-dimethyl-4-(2-nitrophenyl)-3,5-pyridine carbonic acid dimethylester, $C_{17}H_{18}N_2O_6$) has already given rise to a plurality of potent derivatives, the so-called second generation dihydropyridines, Nitrendipin 1,4-dihydro-2,6-dimethyl-4-(3-nitrophenyl)-3,5-pyridine carbonic acid ethyl-methyl ester, $C_{18}H_{20}N_2O_6$ and Nisoldipin isobutyl-methyl-1,4-dihydro-2,6-dimethyl-4-(2-nitrophenyl)pyridine-3,5-dicarboxylate, $C_{20}H_{24}N_2O_6$.

The dosage form of the conventional nifedipin acute dosage form for single doses is, generally speaking, 5 to 10 mg. while the newer dihydropyridine derivatives are at this time, dosed at lower level.

Many galenic developments have been suggested in order to bring dihydropyridine, in particular nifedipin, into the organism at a sufficient speed, by rapidly releasing the active substance from the dosage form. These, however, take into a account a plurality of compromises because on the one hand, the difficult solubility or insolubility of these active substances in a physiological environment provides barriers to or makes more difficult their release from the dosage form. On the other hand, a rapid release is the criterion for the fastest entry into action after dosing. These requirements are not inconsiderable for raising the level of patient compliance.

At the present time the technological methods utilized for the production of dosage forms of dihydropyridine derivatives, in particular nifedipin are as follows:
a) Processing of the active substance with solvating agents (tensides) and additionally
b) Dissolving the active substances in organic solvents, for example polyether alcohols of tetrahydrofurfuryl alcohols.

Because of the light sensitivity of dihydropyridine a conventional, colored soft gelatin capsule may be utilized, for example, as carrier (light protection) for the above mentioned nifedipin solubilisate or nifedipin solution in an organic solvent. After dosing, the nifedipin should be released from the dosage form in finely divided form. Herein however, it must be considered that the active substance is thereafter not really in a free form but must first be released from its complex with the solvating agent which has the disadvantage that it is not sufficiently rapidly available for the organism.

Furthermore, this mode of proceeding also has the possible risk that under physiological conditions, the nifedipin is precipitated in a crude crystalline form as soon as the solvating agent (tenside) is no longer active. Furthermore, the use of tensides or organic solvents is not without problems with respect to toxicological considerations.

Liquid nifedipin preparations which can be utilized in drop form are equally commercially available. Patients particularly like the dosage form of these nifedipin drops, in particular, elderly patients who have found the swallowing of solid formulations (tablets, capsules) to be unpleasant or have difficulties therewith. Furthermore, they have the advantage of accurate dosing.

While the liquid dosage forms (from a technological point of view) are a well conceived dosage form, (the process of the disassociation of solid, "single unit" forms as well as, for example, tablets or capsules is irrelevant), these preparations, with respect to the dihydropyridines are not opportune. In addition to the reasons set forth above (presence of tensides and/or organic solvents), there is further more extensive reason to seek this class of compounds. It is known that dihydropyridines are exceedingly light sensitive and tend to dissociate, in particular in solutions. Thus, particularly during the extraction of the nifedipin drops by the patient from the storage container, one cannot exclude the possibility of a partial dissociation of the nifedipin by the action of light even before administration. Since this dosing, particularly with older patients, is a rather time-consuming process, the risk of dissociation of the active substance before actual intake is considerably increased.

Further, it should be noted that even the storage of solutions of nifedipin for drops, in brown or dark colored glass bottles does not yield sufficient extended storage stability (protection from the action of light). On pharmacological grounds alone, it would be desirable, in fact advantageous, to provide a preparation of dihydropyridine derivations in a rapidly available acute dosage form which as a solution of the active substance. However, because of the physicochemical properties of the active substance as for example insufficient water solubility, light sensitivity in solution and so on, such a goal is either unreachable or only via considerable detours.

The task of the present invention therefore is to provide a dosage form for oral or peroral administration of dihydropyridine derivatives, in particular nifedipin which provides for rapid release of the active substance and overcomes the problems of the state of the art.

SUMMARY OF THE INVENTION

This task is solved by providing dihydropyridine derivative containing pellets which substantially comprise a dispersion of dihydropyridine derivative in a matrix which comprises principally of skeleton former, for example gelatin, fractionated gelatin, collagen hydrolysate and/or a gelatin derivative.

In particular, the present invention makes available dihydropyridine derivative containing pellets characterized by a dispersion of a dihydropyridine derivative in a matrix which is preferably formed from a skeleton former selected from the group consisting of gelatin, fractionated gelatin, gelatin derivatives, collagen hydrolysate and mixtures thereof.

Furthermore, the present invention provides a process for the preparation of dihydropyridine derivative containing pellets, characterized thereby that:

a) a skeleton former selected from the group consisting of gelatin, fractionated gelatin, collagen hydrolysate and gelatin derivatives as well as mixtures thereof are dissolved in a solvent.

b) the dihydropyridine derivative is dispersed in the smallest possible particles in the solution, c) the dispersion of the skeleton former and the dihydropyridine derivative are dropped into an exceedingly cold inert solvent to form the pellets, and d) the pellets are dried.

The molded particles of the present invention require no outer coating (hollow particles as casting molds, etc.) during the formation thereof (molding). The product falls, because of the production process, into the category of free flowing materials. In this, the dihydropyridine derivative is not present in the heretofore known fluid, solvent assisted form but rather in a dry form, whereby an accelerated active substance release from this preparation proceeds under physiological conditions.

The scope of the invention encompasses round unitary molded particles of grain size in the range of 0.2-12 mm. Thus, in dependence upon the dosage process (dropping arrangement), there may be obtained a grain size unity of more than 70%, which by classification, can be further improved. Just this size unity makes the pellets of the present invention particularly suitable for pharmaceutical USES.

The pellets of the present invention posses many advantages over the state of the art.

The active substance lies, incorporated in the carrier skeleton, in totally dry form. Chemical changes, for example by hydrolysis are not possible because of the exclusion of moisture. Furthermore, the corresponding dihydropyridine derivative, in particular nifedipin, is, by these means, advantageously protected from the access of light and thus protected from dissociation. This protection can be further increased where the carrier skeleton (matrix) of the pellets of the present invention comprise, for example, pharmaceutically acceptable, yellow colorants or, in the case of gelatin, gelatin materials, selected for their own particular yellow coloring.

After contact of the molded particles of the present invention with water or a physiological fluid, the carrier skeleton, because of its special properties provided by the present invention, is very rapidly dissolved and the incorporated active substance is liberated. This procedure is of particular importance when one considers that in practice, after oral administration of the pellets of the present invention, the active substance is almost immediately liberated by the action of saliva and thereby is already available for absorption in the oral cavity. Thus, there is provided a substantially more patient friendly alternative to the conventional nifedipin chewable capsules provided by soft gelatin.

Even where no water or other fluids are available for the intake of medicaments, these pellets of the present invention are particularly advantageous. After dissociation of the carrier skeleton as a result of the action of saliva, the residual resultant residue can be very readily swallowed.

The skeleton former of the molded particles of the present invention forms a loose porous network in which the active substance is incorporated. The only condition that must however be provided is that there is no incompatibility between the active substance and the skeleton former. After contact with water or aqueous fluid, for example in a physiological environment, there is penetration into the pores of the network which leads to a very rapid collapse of a previously mechanically stable form. As a consequence thereof the active material is released.

As skeleton formers, there may basically be used all hydrophilic suitably water soluble macromolecular substances as, for example, polysaccharides such as dextran with low average molecular weight (40,000 to 100,000 D), dextrins, alginates (for example sodium alginate), polyvinylpyrrolidone, polypeptides such as gelatin, fractionated gelatin, collagen hydrolysates or gelatin derivatives, combinations and combinations of the foregoing materials in different proportions.

Gelatin is a scleroprotein derived from a collagen containing material which, according to its mode of production, has different properties. It comprises basically four molecular weight fractions whose physico-chemical properties are influenced in dependence upon the molecular weight and the percentage weight proportion. The higher, for example, the proportion of microgel ($10^7$ to $10^8$ D), the higher is also the viscosity to the aqueous solution. Conventional types contain up to 10 wt. %. The fractions of alpha-gelatin and its oligomers ($9.5 \times 10^4/10^5$ to $10^6$ D) are determinative for the gel solidity and generally speaking lie between 10 and 40 wt. %. Molecular weights under that of alpha-gelatin are designated as peptides and in conventional gelatin qualities (low bloom) can comprise up to 80 wt. %.

Preferably gelatins, fractionated gelatins, gelatine hydrolysates or gelatin derivatives, cold water soluble gelatin derivatives or gelatins with a maximum molecular weight distribution below $10^5$ D are utilized as the main components. Particularly preferred are collagen hydrolysates, cold water soluble gelatin derivatives or gelatins with a molecular weight distribution under $10^5$ D. The pellets, surprisingly, dissociate in water at room temperature or in a physiological environment in less than 30 seconds and thus practically release their entire content of active substance.

Particularly in collagen hydrolysates, whose maximum molecular weight distribution is in the range of $10^4$ to $9 \times 10^4$ D or in gelatin, there is found a natural biopolymer which, on the one hand is an inert ingredient which is pharmaceutically recognized and has multiple uses, and on the other hand, the most recent advances in production technology of this material enables constant and reproducible properties to be provided to the molded particles of the present invention. Such skeleton formers yield, for example, the fastest dissociation of the macromolecular skeleton of the pellets of the present invention while maintaining the highest mechanical stability.

Where thus the pellets of the present invention contain active substances of the dihydropyridine group in suitable dosage arrangements (dosage dispensers and the like) which enable the simple, single intake, there is thus produced a acute dosage form which, with respect to stability, dosage form security, handlability and use of the product, substantially exceeds the state of the art.

One is not however restricted to this mode of use. Because of the unitary round form and the flowability qualities associated therewith, there is provided a high level of dosage exactness. These properties and furthermore their high breakage resistance with low friability make these pellets particularly suitable as intermediate products for further process steps. Surprisingly, they may be directly compressed into tablets without any loss of the desirable release properties of the active substance. Such tablets equally have a high breakage resistance with low friability. Surprisingly, they possess yet further new properties. Thus, for example under test conditions (solution test apparatus in accordance with U.S. Pharmacopeia), there is no dissociation process into smaller granular particles as occurs in conventional tablet formulations but rather a total dissolution of the skeleton material, generally within 5 minutes. Clearly, the excellent solution properties of the skeleton matrix are preserved after compression. The tablets are dissolved without the initial dissociation. In contrast thereto, conventional granulate compressed tablets first dissociate into the granulate particles which are dissolved solely subsequently.

It is thus possible for the pellets of the present invention to be utilized for the technological development for other dosage forms in surprisingly varied types and manners.

A further processing, for example charging into hard gelatin capsules, may be readily carried out with high dosage exactness in view of their round and unitary form.

As the pellets of the present invention have high mechanical stability, they can, if desired, be coated with pharmaceutically acceptable film formers, for example, for the achievement of resistance to gastric juices. The combination of coated and uncoated pellets in conventional hard gelatin capsules thus allows the active substance to be released in a pulsed manner.

The combination of pellets which contain active substances of different indication groups makes it possible to provide combined preparations, i.e., through charging into conventional hard gelatin capsules. Appropriate combinations can for example be: dihydropyridine derivatives with beta-sympathicolytics or diuretics.

Other uses are for example, the charging into bags to form drinkable granulates (pellets), or the preparation of the initial dose in sustained release forms, etc.

Thus starting from a single product the molded particles of the present invention, a substantial range of technological applications is provided.

For the formation of the pellets in accordance with the present invention a procedure is suggested which not only permits the use of a plurality of macromolecular materials but furthermore has low technological requirements, while having a readily controlled procedural path and is thus readily and economically carried out.

Further embodiments of the present invention are set forth in the United States application for Letters Patent as set forth herein, whose disclosure is incorporated herein by reference. These parallel U.S. applications have been filed in the United States Patent and Trademark Office by the same inventors on the same day and are as follows:

Title: "Aloe Vera Juice Containing Pellets for Production Thereof and the Use Thereof as Pharmaceutical Cosmetic and Peroral Agents", U.S. Ser. No. 07/876,876.

Title: "Pellets Containing Peptides, Method of Making Same and Use Thereof", U.S. Ser. No. 07/876,865.

Title: "Means for Containing Active Substances Having a Shell of Hydrophilic Macromolecules, Active Substances and Process for Preparation Thereof", U.S. Ser. No. 07/876,864.

Title: "Pellets Containing Plant Extracts, Process of Making Same and Their Pharmaceutical Peroral or Cosmetic Use", U.S. Ser. No. 07/876,866.

Title: "Soft Gelatin Capsules", U.S. Ser. No. 07/876,863.

Title: "Peroral Dosage Form for Peptide Containing Medicaments, in Particular Insulin", U.S. Ser. No. 07/876,867.

In the first step of the process the hydrophilic molecule, in particular gelatins, collagen hydrolysates with gelatin derivatives or mixtures thereof with macromolecules are dissolved in a suitable solvent—water is the solvent choice in most cases. One may, if desired, utilize a certain amount of warming in order to obtain a gelatin sol which, with gelatin, occurs at a temperature of 37° C. or more.

Further inert ingredients or carrier materials such as, for example, filler materials such as lactose, dispersing materials such as disodium hydrogenphosphate, pH-adjusters for example disodium citrate, emulsifiers such as lecithin, stabilizers such as ascorbic acid, cosolvents such as polyethylene glycol, natural colorants for example carotinoides, odorants or flavor adjusters as for example sugar substitutes, complexing agents or chelating agents such as cyclodextrin, may be added.

The concentration ranges of the hydrophilic macromolecules in particular gelatins, collagen hydrolysates or gelatin derivatives are suitably under 30% (weight percent), most suitably 3 to 15% relative to the mass to be utilized without the active substance. Correspondingly, the water content of the entire mass may be up to 70 wt. % or more.

The concentration range of the additional skeleton builders such as for example dextrans, saccharose, glycine, lactose, polyvinylpyrrolidone, in particular mannitol, lie below 30% (weight percent), for example in the range of 0–15% with respect to the worked mass without the active ingredient. Preferably the proportion of the additional skeleton builder is not larger than the proportion of the original skeleton builder.

These materials particularly however mannitol, can act as filling components and improve the stability of the polymer skeleton of the pellets of the present invention and thus also their properties.

In a second step, the dihydropyridine derivative suitably in finely divided form, is dispersed in the solution of the hydrophilic macromolecule.

The system described in the second step now passes through a third molding step, via an appropriate dosing system, into an exceedingly cold readily vaporizable fluid, suitably a bath with liquid nitrogen. Already during the free fall but additionally in the dropping bath, each discrete drop thereby takes on a spherical condition due to the formation of a gas coating because of the surface tension of the system/gas, before total freezing occurs. Just this rapid but nevertheless controlled predictable freezing, fixes the given condition of the system instantaneously, that is to say, that no active substance can diffuse into the surrounding medium, dissolved pharmaceuticals cannot crystallize out anymore, suspensions cannot sediment, emulsions cannot break down, thermally sensitive or moisture sensitive materials are cryoconserved, the carrier skeleton cannot shrink and so on. The production procedure with inert fluid gas has therefore no disadvantageous influence and does not cause alteration of the product which is a considerable advantage. The desired properties are maintained.

As a dosage system there may used all arrangements which produce discrete regular drops of predeterminable size, for example pipette type dropping arrangements, suitable spray and dust jets or peristaltic pumps.

A preferred embodiment of the present invention comprises a procedure utilizing the Cryopel ® dosage system developed by Messer Griesheim GmbH (based on DE OS 37 11 69). In combination with a drop freezing arrangement, the Cryopel ® apparatus makes the scaling up of the process of the present invention particularly simple. This arrangement which can be driven with liquid nitrogen distinguishes itself particularly well economically. The freezing yield depends on the nature of the product but can come up to 30 l per hour. This arrangement, because of its desirable dimensions and particularly because of the sterile nature of the proceeding, can be utilized everywhere. Continual production methods with little maintenance and cleaning requirements make possible the economic conversion of the process invention to an industrial scale. Production scale arrangements are already in operation and give as yield of over 400 kg. per hour.

BRIEF DESCRIPTION OF THE DRAWINGS

There is shown:

FIG. 1 is a schematic representation of the Cryopel ® process developed by Messer Griesheim GmbH. The matrix mass formed in accordance with the present invention is dropped as drops, via a heated provision arrangement 1 through calibrated jets into the fluid nitrogen bath 3 at about −196° C. and formed into round pellets under simultaneous shock freezing. The frozen products are removed over arrangement 5 via a continuously running transport band 2. The dosing of the liquid nitrogen is carried out via line 7 and the thus produced nitrogen gas is expelled via line 6. Insulation 4 encompasses the entire system.

In FIG. 2 is a schematic representation of the process wherein the cold matrix mass, which may be heated to a maximum of 70° C. is lead via a controllable dosage pump 8 over line 9 in a continuous manner through the heatable dropping jet 10 and dropped into the insulated bath 11 containing liquid nitrogen 12. The shock frozen pellets are removed batchwise. This arrangement permits the processing of highly viscous masses.

Figure 1:
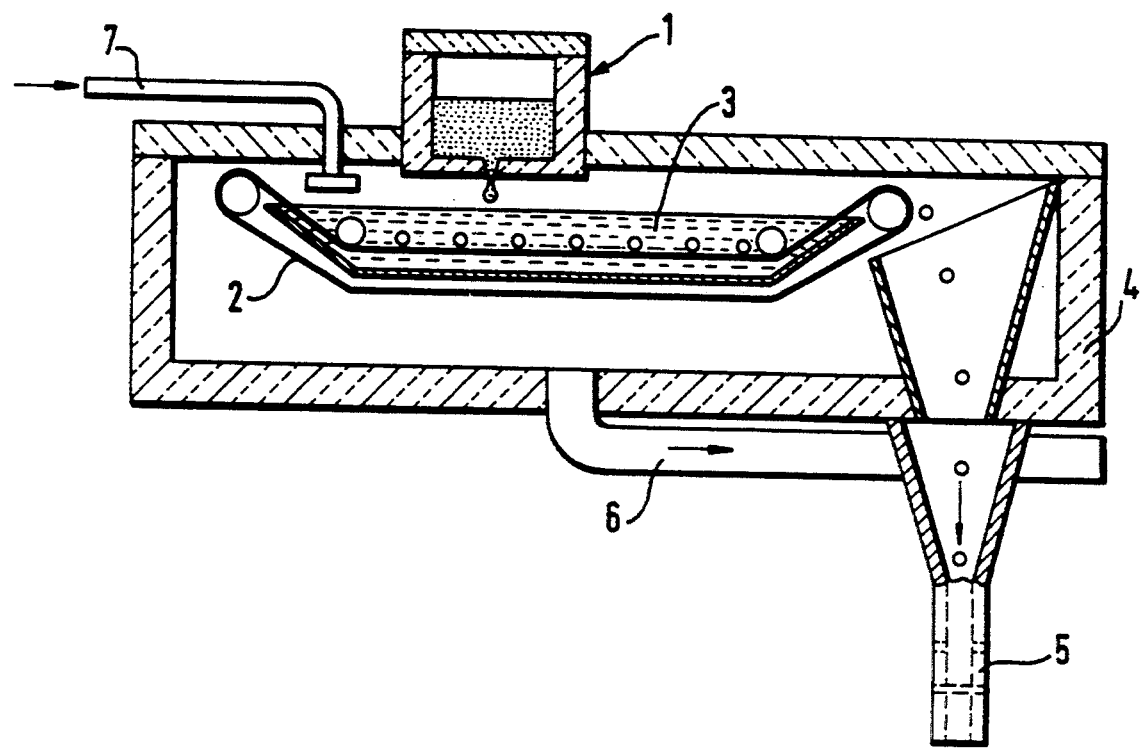
FIG. 1—A schematic representation in cross sectional elevation of an arrangement for carrying out the process of the present invention.
Figure 2:
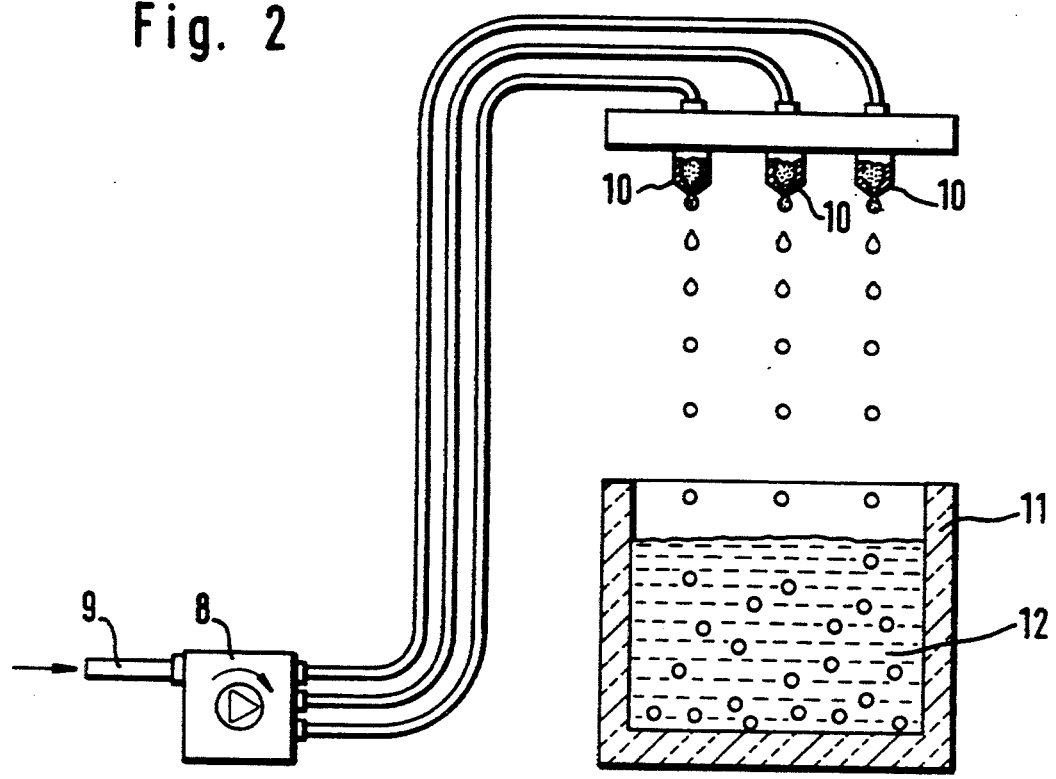
FIG. 2—A further arrangement for carrying out the process of the present invention in schematic illustration.

Where the system to be processed is not sufficiently capable of flowing or forming drops, or one can, for example, add additional amounts of water of between 1 and 10 wt. %, the processing temperature may be raised or pressure may be utilized in the dosage step. In the contrary case, where for example the system has too low a viscosity, analogously, reduced pressure may be utilized. This mode of proceeding provides a regular formation as well as separation of individual drops.

The processing temperature may be varied across a wide range. Preferably this should lie under 80° C., in the case of gelatin.

Thus, substances of widely varying viscosity may be processed without any difficulty, for example utilizing the Cryopel ® dosing mass, one can readily operate in the viscosity area of $1 \times 10^{-3}$ to 12.5 Pa seconds.

Additional very cold fluids which may be utilized for the process of the present invention include for example, liquid inert gases for example, argon.

In dependence upon the dosage system chosen a grain size unity of over 70% can be achieved, which can be increased through classification. Just this unique property of pellets of the present invention makes them suitable as a pharmaceutical technological basic form, for example a dosage form with respect to conventional pellets and makes possible the provision of single unit dosage forms (i.e., pellets of 0.4 to 22 mm. diameter).

The frozen pellets, after production or after the drying process (see below) are classified, when this is necessary in order to provide a reproducible grain size. Undesired sizes can again be introduced into the general process so that a loss free or substantially loss minimized procedure is provided by recycling.

In the fourth process step, the frozen pellets are transferred to a freeze drying arrangement. It is however possible to store the product meanwhile at a low temperature, for example −30° C.

The sublimation of the solid (frozen) solvent by freeze drying yields to the end product. The carrier material builds a network with fine channels and pores.

The dried pellets are removed from the freeze drying arrangement and can be processed further.

By carrying out the process of the present invention, it is sufficient in the simplest case, to provide an aqueous gelatin solution with the gelatin of the prescribed specifications, to suspend a nifedipin, that is to say, the dihydropyridine derivative in finely crystalline and homogeneous form, and to drop the entire system via a suitable dosage arrangement into a dropping bath provided with liquid nitrogen. The deep frozen pellets formed in this manner are thereafter converted into a dry state by lyophilization.

In the framework of the present invention it has been shown advantageous to precipitate finely divided dihydropyridine from a .solution of dihydropyridine with a water miscible and pharmaceutically acceptable organic solvent such as alcohol, directly into the gelatin solution. After removal of the alcohol (for example, by evaporation) one proceeds in a manner analogous to that described above to provide the molded particles of the present invention.

For the already mentioned combination preparations, dihydropyridine derivatives may for example be combined with beta-sympatholytics or diuretics.

In the case of optically active substances, there may be utilized the racemates as well as the enantiomeric components and mixtures thereof.

The following examples exemplify the invention.

All procedures with dihydropyridine derivatives have to be carried out under yellow light (to protect against dissociation).

EXAMPLE 1

Active substance: Nifedipin
Prescription for the basic working mass:
300 g. collagen hydrolysate
750 g. mannitol 3950 g. distilled water The collagen hydrolysate and the mannitol are dissolved in distilled water under stirring. Into this solution there are homogenized 100 g. of micronized nifedipin, where desired, with the addition of conventional pharmaceutically acceptable inert ingredients.

After defoaming under vacuum, the suspension is dropped at room temperature via a Cryopel ® dosage arrangement, into a dropping bath of liquid nitrogen to form the pellets.

During subsequent freeze drying, the water is removed to provide, after classification, round molded particles with a mean nifedipin content of 2 mg.

These molded particles dissociate in water at room temperature (dissolution test apparatus in accordance with the United States Pharmacopeia, test medium 100 ml. water, 23° C.) completely within 20 seconds and contain nifedipin in free form.

The dried molded particles are charged to a dark colored dosage container in which they are protected from the impact of light and can be removed in the desired dosage amounts.

EXAMPLE 2

The dried molded particles of Example 1 are directly pressed on an excentric press into tablets with a mean nifedipin content of 10 mg.

In a dissolution test apparatus in accordance with the United States Pharmacopeia (900 ml., 0.1N HCl, paddle, 75 rpm, 37° C.), there is a total solution of the tablet and release of the active substance within 5 minutes.

The pellets of Example 1 can alternatively, be charged to opaque hard gelatin capsules with a mean nifedipin content of 5 mg.

EXAMPLE 3

The prescription for providing the basic working mass of Example 1 is altered in the following manner:
300 g. collagen hydrolysate
60 g. polyvinylpyrrolidone K 15
100 g. saccharose
2540 g. distilled water.

The further process of working follows that of Example 1.

We claim:

1. Dihydropyridine derivative containing dried cryopellets comprising a pharmacologically effective amount of a dihydropyridine derivative, the amount and activity whereof being essentially undiminished by the cryopelleting, dispersed in a matrix at least 50% w/w whereof comprising substantially of skeleton forming water soluble hydrophilic macromolecular material having a maximum molecular weight distribution under $10^5$ D selected from the group consisting of gelatin, fractionated gelatin, succinylated gelatin, collagen hydrolysates, and mixtures thereof.

2. Dried cryopellets in accordance with claim 1 further comprising at least one additional skeleton forming hydrophilic material.

3. Dried cryopellets in accordance with claim 1 further comprising at least one additional skeleton forming hydrophilic material selected from the group consisting of dextran, sugar, glycine, lactose, sorbitol, mannitol, polyvinylpyrrolidone, and mixtures thereof.

4. Dried cryopellets in accordance with claim 3 wherein said matrix comprises less than 50 wt. % of said additional skeleton forming hydrophilic material.

5. Dried cryopellets in accordance with claim 1 wherein said matrix further comprises a pharmaceutically acceptable inert ingredient or carrier material.

6. Dried cryopellets in accordance with claim 1 having a particle size of 0.2-12 mm.

7. Dried cryopellets in accordance with claim 1 existing as a lyophilisate.

8. Dried cryopellets in accordance with claim 1 which are rapidly dissolvable in aqueous media wherein said matrix comprises substantially collagen hydrolysate, a cold water soluble succinylated gelatin.

9. Dried cryopellets in accordance with claim 8 wherein the dihydropyridine derivative is selected from the group consisting of N-nifedipin, Nitrendipin or Nisoldipin.

10. Process for the preparation of dried cryopellets having a matrix containing dihydropyridine derivatives the amount and activity whereof being essentially undiminished by the cryopelleting comprising the steps of:
    a) dissolving a first skeleton forming hydrophilic macromolecular material having a maximum molecular weight distribution under $10^5$ D selected from the group consisting of gelatin, fractionated gelatin, succinylated gelatin, collagen hydrolysates and mixtures thereof in water,
    b) dispersing said dihydropyridine derivatives as finely divided particles in the thus formed solution,
    c) forming drops of the thus produced mixture of macromolecular material exceedingly cold inert fluid of density of less than that of the said droplets, at a temperature of between −70° and −270° C. whereby cryopellets are formed and
    d) drying said pellets wherein said first skeleton forming material comprises at least 50% by weight of said matrix.

11. A process according to claim 10 wherein the cold fluid is liquid nitrogen.

12. A process according to claim 10 wherein said drops are of predetermined regular shape produced from a dosing system capable of producing same.

13. A process according to claim 10 wherein the pellets are freeze dried after step d).

14. A process according to claim 10 wherein in step a), to the solution there is added at least one additional skeleton forming hydrophilic material selected from the group consisting of dextran, sugar, glycine, lactose, sorbitol, mannitol, polyvinylpyrrolidone and mixtures thereof the quantities of the first skeleton forming materials of step (a) and the additional skeleton forming material being predetermined to provide, in the dried cryopellets, at least 50% w/w of the matrix, as the first skeleton former.

15. Acute dosage form containing pellets in accordance with claim 1.

16. The process of compressing the dried cryopellets of claim 1 into tablets.

17. The process of converting the dried cryopellets of claim 1 for the formation of gastric juice resistant dried cryopellets.

18. The process of inserting the dried cryopellets of claim 1 into hard gelatin capsules.

19. The process of charging the dried cryopellets of claim 1 into bags for use as drinking granules.

* * * * *